US012645196B1

(12) United States Patent
Greenawalt et al.

(10) Patent No.: US 12,645,196 B1
(45) Date of Patent: Jun. 2, 2026

(54) SYSTEM FOR GENERATING CUSTOMIZED ORTHOPEDIC PILLOW

(71) Applicant: Foot Levelers, Inc., Roanoke, VA (US)

(72) Inventors: Kent S. Greenawalt, Roanoke, VA (US); Jamie L. Greenawalt, Roanoke, VA (US); Chad Warren, Roanoke, VA (US)

(73) Assignee: Foot Levelers, Inc., Roanoke, VA (US)

( * ) Notice: Subject to any disclaimer, the term of this patent is extended or adjusted under 35 U.S.C. 154(b) by 0 days.

(21) Appl. No.: 19/253,490

(22) Filed: Jun. 27, 2025

(51) Int. Cl.
| | |
|---|---|
| *G05B 19/4097* | (2006.01) |
| *A47G 9/10* | (2006.01) |
| *A61B 5/107* | (2006.01) |
| *B33Y 50/00* | (2015.01) |
| *B33Y 80/00* | (2015.01) |

(52) U.S. Cl.
CPC ....... *G05B 19/4097* (2013.01); *A47G 9/1081* (2013.01); *A61B 5/1077* (2013.01); *A61B 5/1079* (2013.01); *A47G 2009/1018* (2013.01); *B33Y 50/00* (2014.12); *B33Y 80/00* (2014.12)

(58) Field of Classification Search
CPC .............. G05B 19/4097; A47G 9/1081; A47G 2009/1018; A61B 5/1077; A61B 5/1079; B33Y 50/00; B33Y 80/00
See application file for complete search history.

(56) References Cited

U.S. PATENT DOCUMENTS

| | | |
|---|---|---|
| 2019/0307269 A1 | 10/2019 | King |
| 2022/0015558 A1 | 1/2022 | Davis et al. |
| 2023/0404286 A1 | 12/2023 | Prince |

FOREIGN PATENT DOCUMENTS

| | | | | |
|---|---|---|---|---|
| CN | 115230164 A | * 10/2022 | ........... | B29C 64/393 |
| EP | 2196173 A2 | * 6/2010 | ............. | A42B 3/124 |

OTHER PUBLICATIONS

English Translation of "CN-115230164-A" (Year: 2022).*
Application No. PCT/US2025/035782, International Search Report and Written Opinion dated Sep. 15, 2025.

* cited by examiner

*Primary Examiner* — Charles R Kasenge
(74) *Attorney, Agent, or Firm* — Woods Rogers Vandeventer Black PLC; Nathan A. Evans

(57) ABSTRACT
System for automatically designing orthopedic pillow based on data sets from scans of both an individual's head-and-neck region and an individual's foot or feet.

17 Claims, 2 Drawing Sheets

2002

2003

2000

2001

SYSTEM FOR GENERATING CUSTOMIZED ORTHOPEDIC PILLOW

BACKGROUND

The present invention relates generally to generating a customizable pillow, including, in cases, automatically generating a design and selecting materials for an orthopedic pillow based on thousands of data points compiled from one or more scans of (a) the patient's head-and-neck regions and (b) the patient's foot or feet. In aspects, the pillow can be designed to help improve sleep while providing proper cervical alignment and reduce pain.

The present invention relates to a system for customizing a pillow design to an individual's orthopedic needs, the system comprising, in embodiments:

> an infrared scanner, a three-dimensional scanner, a digital scanner, or combinations thereof, which scan one or more portions of an individual's foot or feet to provide a first set of data points;
>
> an infrared scanner, a three-dimensional scanner, a digital scanner, a goniometer scanner, or combinations thereof, to scan one or more portions of an individual's head and neck region to provide a second set of data points;
>
> a processor, and a storage having encoded thereon executable instructions that, when executed by the processor, cause the processor to carry out:
>
>> generating inputs based on both the first set of data points and the second set of data points; and
>>
>> applying the generated inputs to a set of pre-determined parameters chosen to treat orthopedic needs using a pillow, to define a shape, size, or design of the customized pillow and to select one or more materials to be used to render the customized pillow, thereby generating a virtual pillow customized to the individual to treat the individual's orthopedic needs.

In aspects, the system can analyze tens of thousands, dozens of thousands, or hundreds of thousands of data points of the neck, head, and/or shoulders using a head-and-neck region scan along with a foot or feet scan, and optionally patient information, to create a uniquely custom therapeutic pillow effective for both side and back sleepers.

Nearly one-third of Americans suffer from at least one sleep disturbance, and the Centers for Disease Control has reported that 20 to 25 percent of Americans have chronic pain. In a randomized controlled trial, Lee et al. (2021) showed that ergonomic pillows significantly reduced neck pain and improved sleep efficiency in patients with chronic pain. An optimal sleep position has also been shown to help interrupt nociceptor input, thus decreasing pain. These findings underscore the importance of tailored interventions in addressing the interplay between spinal alignment, sleep, and pain. (See, e.g., Sochal, M., Ditmer, M., Turkiewicz, S. et al., The effect of sleep and its restriction on selected inflammatory parameters. Sci. Rep. 14, 17379 (2024); see also, Lee, J. Y., et al. (2021), Effect of ergonomic pillows on sleep quality and cervical pain: A randomized controlled trial. Journal of Clinical Sleep Medicine, 17(3), 345-352.)

Accordingly, there is a need for an automatically-designed customized pillow optimal or enhanced to support a patient's preferred sleep posture. Chronic pain, inflammatory responses, and serial distortions can all be helped using the pillow as described herein and, in some cases, reversed with proper support from a customized pillow as explained herein.

The invention described herein improves upon problems with currently-existing systems and methods. A significant problem is lack of accuracy and precision of 3D scans, as scan accuracy can be affected by patient movement, clothing, and the type of scanner used. Inaccuracies in the scan data can lead to a poorly fitting pillow.

Further problems include the fact that current materials may not offer the ideal combination of support, comfort, and breathability, for example. According to aspects of the current invention, the system can automatically decide and select material that will better serve the patient orthopedically, or increase a comfort level for the patient when using the pillow. For example, memory foam can trap heat, while latex may be too firm for some users. Based on the scans and/or patient input, the current invention can, in aspects, further suggest and/or choose a material or materials to make the customizable pillow.

Another problem in the current state of technology is that the existing design algorithms do not fully capture the complex biomechanics and kinetic chain of the head, neck, and spine. Over-simplification can result in suboptimal support.

Indeed, even with measurements and designs, some patients find currently-existing pillows uncomfortable or difficult to adjust to. Data Security and Privacy is also an issue, as handling sensitive patient data (e.g., 3D scans) requires robust security measures to protect privacy and prevent unauthorized access.

Therefore, a need exists for an improved system for automatically designing a pillow using an automated system and manufacturing the customizable pillow based on the patient scans and/or patient input.

SUMMARY

The present invention provides a system for automatically designing a customized orthotic pillow having, for example, restorative aspects for patients who can benefit from a design that contours to the natural curvature of each patient's cervical spine, promoting even weight distribution and reducing pressure points, by way of example. Maintaining this neutral neck position can minimize strain and prevent exacerbation of pain during sleep for conditions like cervical stenosis. By way of example, the customized pillow can accommodate patients with sleep apnea by cutting out a portion of the well for the mask from their CPAP machine to fit comfortably without adjusting their sleeping position.

In aspects, the design based on the system can also be flipped over to a recovery side, which, in aspects, can be flat to help accommodate pain scales for extreme problems like whiplash. The design can also address more common issues such as back pain, neck and shoulder pain, forward head posture ("tech neck"), tension headaches, arthritis, and other conditions associated with poor posture.

Additionally, a specially-designed pillow, such as one using memory foam, on the recovery side, can aid patients suffering from conditions like whiplash. The recovery side may, in designs, provide slight flexion to help with pain relief while inflammation persists. It can be used in conjunction with ointment or ice-pack treatments to reduce swelling during a patient's initial healing. In aspects, the pillow can be flipped back to the restorative side for long-term treatment, providing slight traction during the recovery/rehab phase and preventing stiffness and pain. It is also envisioned that both sides of the pillow are recovery sides, or wherein both sides are restorative sides.

The customized pillow can be tailored to a patient suffering from, for example, cervical stenosis. The dual-patient scan described herein can facilitate custom design that also considers a patient age as a guideline for predicting degenerative changes in the spine and adjust accordingly. For example, for patients with cervical stenosis, the pillow can help relieve pressure on the spinal cord and hold the chiropractic adjustment. Spinal stenosis is a condition that requires the patient to sleep on the restorative side with their head more flexed or on an incline. Sleeping flat would be uncomfortable and painful for a stenosis patient and could cause neurological symptoms. In this aspect, entering patient parameters, such as age, can help aid in the design of the generated virtual pillow and ultimately-manufactured pillow.

Due to the system explained herein, wherein the system scans the foot or feet of the patient and also scans a head-and-neck region, combining data sets from those scans of the different regions to develop the customized pillow as made from, in aspects, an optimized, rendered virtual pillow, the system can more safely and effectively treat individuals who are using pillows designed based on existing pillow design technology. In an example, the head and neck (and in cases shoulders), can be scanned with the "Posture Check 3D" scanner, which, in aspects, measures 130,000 three-dimensional data points of the patient's neck, head, and shoulder dimensions, including the severity of a patient's forward head posture, by way of example. In further aspects, additional information can be used to inform the pillow design, including but not limited to a patient's age, a patient's weight, a patient's preferred sleeping position, and/or natural respiratory issues, like snoring. The pillow can be designed in many sizes, including, by way of example only, travel, standard, queen, and king.

In other embodiments, the pronation stability index and forward head posture scans can be used to analyze over 400,000 data points for a custom report of findings. In aspects, more than 130,000 of those data points are used as part of the process to create the customized pillow, designed to aid in, for example, the patient's recovery sleep cycle and is a way to treat patients who suffer from various health problems associated with serial distortion and sleep disturbances. The custom pillow can also help to mitigate nociceptor input for pain and proprioceptor and mechanoreceptor input for position, pressure, and imbalance. By incorporating these strategies into clinical practice, healthcare providers can help ensure patient compliance, improve patient outcomes, enhance quality of life, and foster long-term recovery.

BRIEF DESCRIPTION OF THE DRAWINGS

The accompanying drawings illustrate certain aspects of some of the embodiments of the present invention and should not be used to limit or define the invention. Together with the written description the drawings serve to explain certain principles of the invention. For a fuller understanding of the nature and advantages of the present technology, reference is made to the following detailed description of preferred embodiments and in connection with the accompanying drawings, in which.

DETAILED DESCRIPTION

Figure 1:
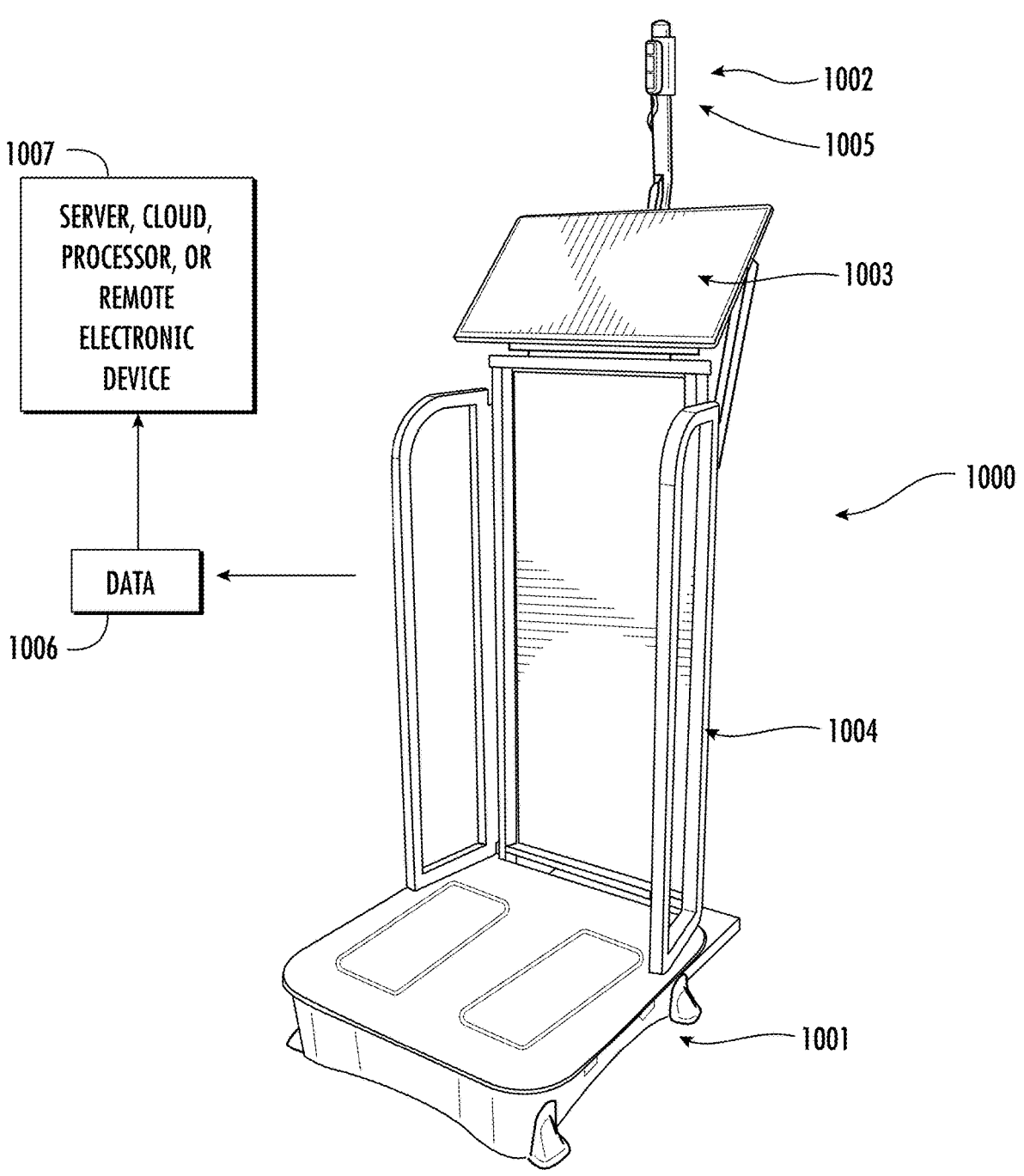
FIG. 1 shows a depiction of the apparatus and/or system according to embodiments as described herein.

The present invention provides a system for scanning and extrapolating from the scans links and relationships between a human kinetic chain between the feet and the head-and-neck region of the scanned individual. Using the scan data sets from both the patient's feet and head-and-neck region, the system can create, in embodiments, a virtual representation of the patient's posture, kinetic chain, orthopedic needs, skeletal relationships, areas of concentrated pressure, and/or structural abnormalities, in the patient's skeleton or body, that cause uneven weight distribution, areas of reduced or absent pressure, muscle weakness, issues of asymmetry by comparing pressure distributions, unequal leg lengths, muscle imbalances, discrepancies in weight distribution between the left and right sides of the body and/or related to body parts, and/or limited ranges of motion in different limbs and/or body parts. By creating a specialized pillow for the patient using data sets from both the foot scan and the head-and-neck region scan, the pillow can be designed to, among other things:

Offload High-Pressure Areas: Redistribute pressure away from painful or vulnerable areas;

Support a proper arch and/or head angle relative the neck, shoulders, and/or body; and/or Correct Biomechanical Abnormalities.

Using the scan data sets from both the patient's feet and head-and-neck region, and in aspects, other aspects of the patient's anatomy, the system can be used to automatically design the customizable pillow. In cases, the system can then compare the scan data sets to the generated virtual representation of the patient to known information on a pillow design/geometry, and in cases materials to make the pillow. In aspects, this cross-referencing of the scans to pillow designs is used to design a specific virtual pillow customized to the patient's orthotic need(s) based on data sets from the at least two scans, and make a real pillow from the automatically generated virtual pillow.

For the Head-and-Neck Region

By way of example, structured light scanners, laser scanners, and/or photogrammetry, can be used to capture the geometry of the patient's head, neck, and/or shoulders. These scanners can create a digital 3D model by projecting light patterns or lasers onto the body and analyzing the distortions or by using multiple photographs to reconstruct the shape, such as of the head, neck, and/or shoulders, of the patient. In aspects of the invention described herein, the patient's head-and-neck region is scanned standing, or, in aspects, in a supine or lateral posture. The scan data is then processed to create a detailed 3D model of the head-and-neck region using data points from the scan.

For the Foot or Feet

Various methods and combinations of methods can be used to capture the 3D geometry of the foot and related information about the patient's body, as described herein, including but not limited to (some or all of these can also be used for and related to the head-and-neck region scan):

Pressure Mapping Systems, which integrate with scanning to capture pressure distribution data in addition to the 3D geometry.

Structured Light Scanners, which project a light pattern onto the foot and analyze the distortions to create a 3D model.

Laser Scanners, which use a laser beam to scan the foot's surface.

Photogrammetry, which uses multiple photographs of the foot from different angles to reconstruct a 3D model.

Using one or more of the above methods, the patient's foot or feet can be scanned, either in a weight-bearing or non-weight-bearing position. The scan data sets can be processed to create a digital 3D model of the patient's posture and improper cervical alignment, often including features like deformities, asymmetries, weight distribution issues, body part length differences, and/or body part and skeletal relationships, which could present as orthopedic needs to be treated by the customized pillow.

In aspects, the scan data can further be used for:

Automatic identification of anatomical landmarks;

Arch height measurement and analysis;

Pressure distribution mapping;

Gait analysis integration; and/or

Customizable design templates.

Creating Virtual Orthopedic Pillow Based on Both the Head-and-Neck Region Scan and the Foot or Feet Scan Based on the system described herein, the 3D data sets from the head-and-neck region scan and the feet scan, computer-aided design ("CAD") software can be used to design the custom pillow. Computer-aided manufacturing ("CAM") software then can generate the toolpaths for manufacturing. The orthopedic pillow can be designed to provide specific support, correction, or accommodation based on the patient's foot structure, head-and-neck region structure, biomechanics, body posture, cervical alignment, musculoskeletal relationships, and/or orthopedic needs, as specifically identified and used by the system to automatically generate a customized pillow to treat the patient. In aspects, the CAD design is converted into machine instructions (G-code) for a CNC milling machine or 3D printer.

In addition to designing a geometry or design of the pillow, a wide range of materials are available for the system to select from, depending on the desired properties of the pillow, including but not limited to:

Memory Foam: Viscoelastic polyurethane foam that conforms to the shape of the head and neck.

Down: The soft, fluffy feathers from ducks or geese; known for being lightweight, warm, and moldable.

Feathers: Can be less soft than down and more prone to poking through the cover. Often mixed with down.

Down Alternative (Synthetic Fill): Usually made from polyester fibers, designed to mimic the properties of down.

Latex: Natural or synthetic rubber foam.

Polyester Fiberfill: A common and inexpensive synthetic fill. Comes in various forms, such as clusters or strands.

Microbeads: Polystyrene beads, which can conform to the shape of the head and neck.

Considerations of material properties can include but are not limited to: Flexibility/Rigidity: To control motion and provide support.

Cushioning: To cradle the head-and-neck region in the right place(s).

Durability: To withstand wear and tear.

Weight: To minimize bulk and improve comfort.

Manufacturing Processes of the Actual Pillow Based on the Automatically Designed Virtual Pillow can Include but are not Limited to:

CNC Milling: A block of material is carved into the desired shape using a CNC milling machine.

3D Printing (Additive Manufacturing): The pillow is built layer by layer.

Thermoforming: A sheet of material is heated and then molded over a positive model (e.g., created or informed from the scan data).

Hand Fabrication: Traditional techniques involving manual shaping, grinding, and assembly of materials.

In aspects, the CAD or similar design programs can be used to design the pillow based on the neck-and-shoulder region scan data set in combination with the foot scan. In aspects, the CAM software can be used to translate the design into machine instructions for manufacturing, such as by 3D printing, additive manufacturing, or otherwise having the pillow made based on the virtual pillow automatically designed by the system described herein.

Software and Algorithms:

Technology: Specialized software analyzes the at least two scan data sets, from the feet and the head-and-neck region, to determine the optimal pillow shape and support characteristics. Algorithms may incorporate biomechanical models to predict pressure distribution and spinal alignment. In aspects, the software identifies key anatomical landmarks and relationships, calculates an ideal or improved support profile for the head, neck, and/or shoulder region(s) of the patient, to generate a custom pillow design. In aspects, this can be accomplished by processing the data sets input and, in aspects, patient information input, and comparing or contrasting to known designs of pillows, by way of example, to return as an output information to design a virtual pillow which will treat some or all of the patient's orthopedic needs, which can then be used to manufacture an actual pillow, based on the virtual pillow, for the patient's use.

In other aspects, user testing and feedback gathered from the patient can be used to refine pillow designs and/or properties, such as whether the patients sleeps on his/her back or side, how soft or hard the patient likes his/her pillow, and/or how cool or warm the pillow should be. In other aspects, the patient can enter information, to be used along with the at least two scan data sets, which can further aid in the design of the pillow, such as areas of pain experienced by the user, medical history, sleeping preferences, pillow preferences, injuries, and other issues experienced by the patient that may be used to assist with pillow design geometry and properties.

In other aspects, the invention includes implementing encryption, access controls, and data anonymization techniques, to ensure compliance with relevant regulations (e.g., HIPAA).

In aspects, the system can use foot or feet scan(s) combined with head-and-neck region scan(s), that allow patients to perform scans at home using smartphones or tablets computers, by way of example. The scan data sets can then be transmitted to a manufacturer for remote pillow design and production.

By addressing these limitations and exploring new technologies, it is possible to create orthopedic pillows that are more accurate, comfortable, and effective in promoting spinal health and improving sleep quality. And, based on the system of the present invention, a custom pillow with, among other things, an appropriate style, loft, and incline, can be prescribed to treat the orthopedic needs of the patient, including pain.

Figure 2:
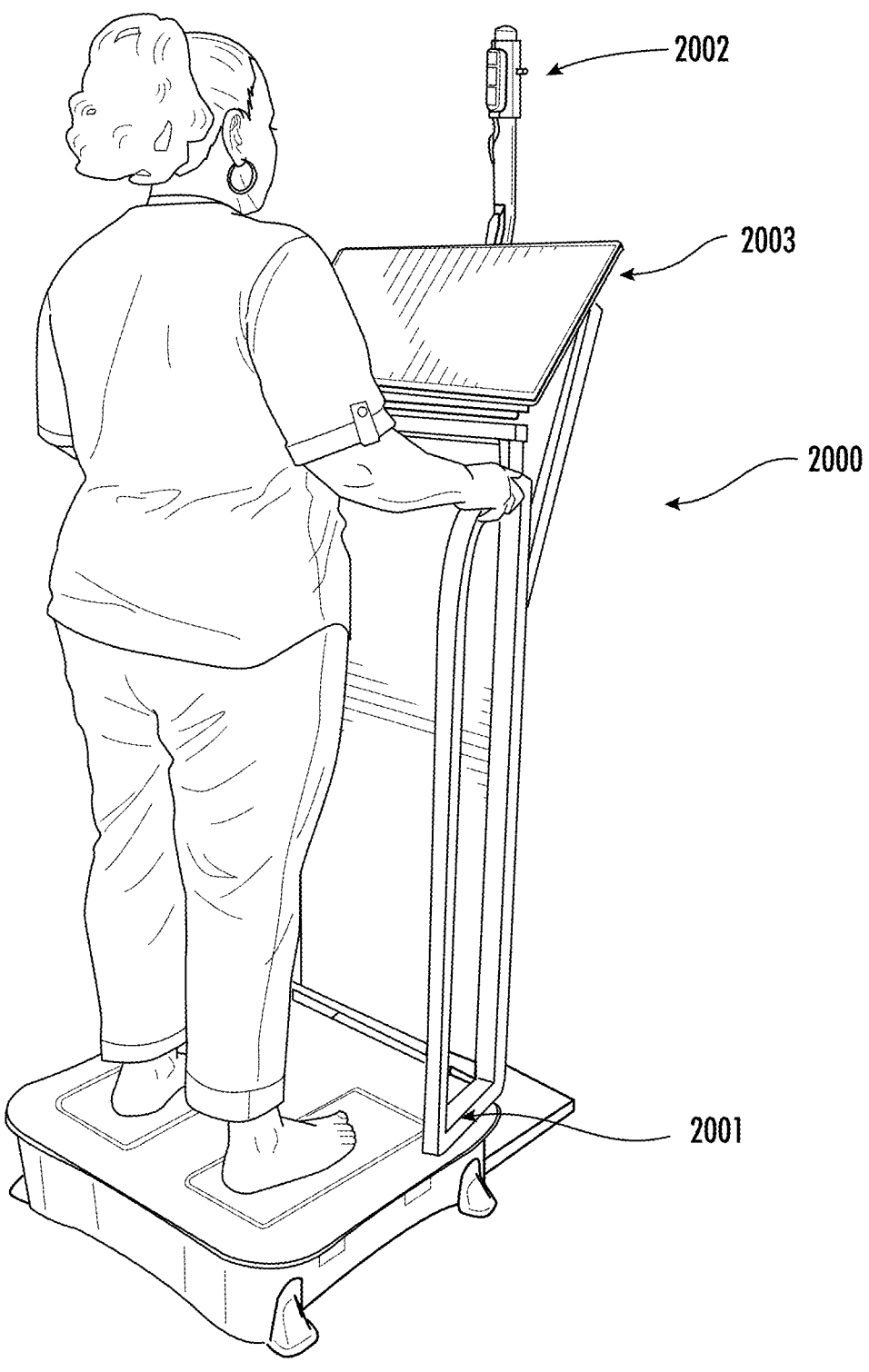
FIG. 2 shows a depiction of the apparatus and system according to embodiments as described herein, wherein an individual is using the apparatus and/or system.

Turning now to the Figures, FIG. 1 shows an embodiment of the current invention, including the overall system and apparatus 1000. Also depicted is the infrared scanner, the three-dimensional scanner, the digital scanner, or combinations thereof to scan one or more portions of an individual's foot or feet 1001. As described herein, the system and apparatus can also use another infrared scanner, three-dimensional scanner, digital scanner, goniometer scanner, or combinations thereof, to scan one or more portions of an individual's head-and-neck region 1002. In aspects, the apparatus or system can include a display screen, such as a touch screen, where an individual can enter personal details and preferences, as well as receive real-time or substantially real-time feedback 1003. The system and apparatus can also include on-device electronics as described herein an below, such as a processor, controller, and/or power source 1004. In aspects, the apparatus and system include a camera for photographic and/or video purposes 1005. In aspects, the apparatus or system can send data 1006, such as data sets or inputs, to a server, the cloud, a separate processor, an additional processor (or wherein the processor is located remotely), or a remote electronic device, such as a cellular phone, computer, tablet computer, laptop computer, desktop computer, and other electronic device(s) 1007. FIG. 2 shows the system or apparatus 2000 being used by an individual, further showing the infrared scanner, the three-dimensional scanner, the digital scanner, or combinations thereof to scan one or more portions of an individual's foot or feet 2001. FIG. 2 also shows the infrared scanner, three-dimensional scanner, digital scanner, goniometer scanner, or combinations thereof, to scan one or more portions of an individual's head-and-neck region 2002. In aspects, as noted herein, the apparatus or system can include a display screen, such as a touch screen, where an individual can enter personal details and preferences, as well as receive real-time or substantially real-time feedback 2003.

The system disclosed herein includes several Aspects, as listed below.

Aspect 1: A system for customizing a pillow design to one or more orthopedic needs of an individual, the system comprising:

a first scanner operative to scan one or more portions of a foot or feet of the individual and generating a first set of data points;

a second scanner operative to scan one or more portions of a head-and-neck region of the individual and generating a second set of data points;

a processor, and a computer-readable medium having executable instructions stored thereon, such that, when the executable instructions are executed by the processor, the processor is operative to:

generate inputs based on both the first set of data points and the second set of data points;

apply the generated inputs to a set of pre-determined parameters chosen to treat one or more orthopedic needs using a pillow;

electronically generate a design of a customized pillow based on the applied generated inputs to the set of pre-determined parameters;

electronically select one or more materials to be used to make the customized pillow; and render a virtual pillow customized to the individual to treat the one or more orthopedic needs of the individual.

Aspect 2: The system of Aspect 1, further comprising: manufacturing a physical version of the customized pillow using the virtual pillow rendering as a template or a model.

Aspect 3: The system of Aspect 2, wherein the rendering of the virtual pillow is electronically performed using computer-aided design ("CAD") software, and wherein the manufacturing of the customized pillow is based on computer-aided manufacturing ("CAM") software.

Aspect 4: The system of Aspect 1, wherein the virtual pillow rendering is used to create a physical version of the customized pillow using three-dimensional printing, additive manufacturing, subtractive manufacturing, computer numerical control ("CNC") milling or manufacturing, thermoforming, hand fabrication, or combinations thereof.

Aspect 5: The system of Aspect 1, wherein the individual's one or more orthopedic needs are or are related to an individual's whiplash, pain, chronic pain, deformities, neck pain, headaches, back pain, sleep disorder, sleep disturbance, nociceptor input pain, spinal misalignment, inflammation, serial distortions, problems balancing, pressure point pain, uneven weight distribution, sleep apnea, snoring, cervical stenosis, forward head posture, tension headaches, arthritis, or combinations thereof.

Aspect 6: The system of Aspect 1, wherein a first side of the customized pillow is a recovery side for treating immediate one or more orthopedic needs of the individual, and wherein a second side of the pillow is a restorative side for longer-term treatment of the one or more orthopedic needs of the individual.

Aspect 7: The system of Aspect 6, wherein the restorative side of the customized pillow is configured to relieve pressure on a spinal cord of the individual, to maintain a chiropractic adjustment, or both, and wherein a geometry of the restorative side of the customized pillow, one or more contours of the restorative side of the customized pillow, or both, are, in whole or in part, based on the first set of data points and the second set of data points, inputs generated from the first set of data points and the second set of data points, or both the first set of data points and the second set of data points and inputs generated from the first set of data points and the second set of data points.

Aspect 8: The system of Aspect 6, wherein the restorative side of the customized pillow provides for a geometry, one or more contours, or both, which are configured to cradle a head of the individual at one or more of an angle, a flexed position, or an incline position, and wherein one of or more the angle, the flexed position, or the incline position, are, in whole or in part, determined by the system.

Aspect 9: The system of Aspect 1, wherein the first scanner includes at least one of an infrared scanner, a digital scanner, or a 3D scanner, wherein the second scanner includes at least one of an infrared scanner, a digital scanner, a goniometer scanner, or a 3D scanner, and wherein the first scanner may be different from or identical to the second scanner.

Aspect 10: The system of Aspect 1, further comprising a forward head posture scan providing a third set of data points, and wherein the generated inputs are based on the first set of data points, the second set of data points, and the third set of data points.

Aspect 11: The system of Aspect 1, wherein the processor, and the computer-readable medium having executable instructions stored thereon, such that, when the executable instructions are executed by the processor, the processor is further operative to: generate a virtual representation of all or a part of a body of the individual or a skeleton of the individual using information from the first set of data points and the second set of data points, the inputs generated from the first set of data points and the second set of data points, or both the first set of data points and the second set of data points and the inputs generated from the first set of data points and the second set of data points, related to one or more of said individual's: posture, body posture, head posture, kinetic chain, body ergonomics, body part ergonomics, skeletal ergonomics, musculoskeletal ergonomics, body part relationships, skeletal part relationships, skeletal abnormalities, posture abnormalities, weight distribution, areas of reduced pressure, areas of increased pressure, limb lengths, muscle weakness, asymmetries between body parts, or body abnormalities.

Aspect 12: The system of Aspect 1, wherein the processor, and the computer-readable medium having executable instructions stored thereon, such that, when the executable instructions are executed by the processor, the processor is further operative to: generate a three-dimensional virtual model of the foot or feet of the individual, a spine of the individual, or a skeleton of the individual, using, in whole or in part, the first set of data points, the generated inputs based on the first set of data points, or both.

Aspect 13: The system of Aspect 1, wherein the processor, and the computer-readable medium having executable instructions stored thereon, such that, when the executable instructions are executed by the processor, the processor is further operative to: generate a three-dimensional virtual model of the head-and-neck region of the individual, a spine of the individual, or a skeleton of the individual, using, in whole or in part, the second set of data points, the generated inputs based on the second set of data points, or both.

Aspect 14: The system of Aspect 1, further comprising a pressure mapping scan operative to scan one or more portions of an individual's foot or feet to supplement the first set of data points or to provide a third set of data points for generating inputs.

Aspect 15: The system of Aspect 1, wherein the processor, and the computer-readable medium having executable instructions stored thereon, such that, when the executable instructions are executed by the processor, the processor is further operative to: automatically identify one or more of, anatomy, target anatomy, or anatomical landmarks, and wherein the automatically identified anatomy, target anatomy, or anatomical landmarks, are used to one or more of: (a) identify the one or more orthopedic needs of the individual, (b) further define the design of the customized pillow, or (c) select or assist with the electronic selection of the one or more materials to be used to make the customized pillow.

Aspect 16: The system of Aspect 1, wherein the processor, and the computer-readable medium having executable instructions stored thereon, such that, when the executable instructions are executed by the processor, the processor is further operative to: determine, based on the first set of data points, the second set of data points, the generated inputs, or combinations thereof, a foot or feet structure of the individual, a head-and-neck region structure of the individual, biomechanics of the individual, body posture of the individual, cervical alignment of the individual, musculoskeletal relationships of the individual, or combinations thereof.

Aspect 17: The system of Aspect 16, wherein the processor, and the computer-readable medium having executable instructions stored thereon, such that, when the executable instructions are executed by the processor, the processor is further operative to: use the foot or feet structure of the individual, the head-and-neck region structure of the individual, the biomechanics of the individual, the body posture of the individual, the cervical alignment of the individual, the musculoskeletal relationships of the individual, or the combinations thereof, to render or assist with rendering the customized virtual pillow to provide specific support, correction, or accommodation, to treat the one or more orthopedic needs of the individual.

Embodiments of the invention also include a computer-readable medium comprising one or more computer files comprising a set of computer-executable instructions for performing one or more of the calculations, steps, processes, and operations described and/or depicted herein. In exemplary embodiments, the files may be stored contiguously or non-contiguously on the computer-readable medium.

Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that while certain of the illustrations and figure may be close to the right scale, most of the illustrations and figures are not intended to be of the correct scale.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. A system for customizing a pillow design to one or more orthopedic needs of an individual, the system comprising:

a first scanner operative to scan one or more portions of a bottom of a foot or feet of the individual in a standing or seated position, and generating a first set of data points;

a second scanner operative to scan one or more portions of a head-and-neck region of the individual and generating a second set of data points;

a processor, and a computer-readable medium having executable instructions stored thereon, such that, when the executable instructions are executed by the processor, the processor is operative to:

generate inputs based on both the first set of data points and the second set of data points;

apply the generated inputs to a set of pre-determined parameters chosen to treat one or more orthopedic needs using a pillow;

electronically generate a design of a customized pillow based on the applied generated inputs to the set of pre-determined parameters;

electronically select one or more materials to be used to make the customized pillow; and render a virtual pillow customized to the individual to treat the one or more orthopedic needs of the individual.

2. The system of claim 1, further comprising: manufacturing a physical version of the customized pillow using the virtual pillow rendering as a template or a model.

3. The system of claim 2, wherein the rendering of the virtual pillow is electronically performed using computer-aided design ("CAD") software, and wherein the manufacturing of the customized pillow is based on computer-aided manufacturing ("CAM") software.

4. The system of claim 1, wherein the virtual pillow rendering is used to create a physical version of the customized pillow using three-dimensional printing, additive manufacturing, subtractive manufacturing, computer numerical control ("CNC") milling or manufacturing, thermoforming, hand fabrication, or combinations thereof.

5. The system of claim 1, wherein the individual's one or more orthopedic needs are or are related to an individual's whiplash, pain, chronic pain, deformities, neck pain, headaches, back pain, sleep disorder, sleep disturbance, nociceptor input pain, spinal misalignment, inflammation, serial distortions, problems balancing, pressure point pain, uneven weight distribution, sleep apnea, snoring, cervical stenosis, forward head posture, tension headaches, arthritis, or combinations thereof.

6. The system of claim 1, wherein a first side of the customized pillow is a recovery side for treating immediate one or more orthopedic needs of the individual, and wherein a second side of the pillow is a restorative side for longer-term treatment of the one or more orthopedic needs of the individual.

7. The system of claim 6, wherein the restorative side of the customized pillow is configured to relieve pressure on a spinal cord of the individual, to maintain a chiropractic adjustment, or both, and wherein a geometry of the restorative side of the customized pillow, one or more contours of the restorative side of the customized pillow, or both, are, in whole or in part, based on the first set of data points and the second set of data points, inputs generated from the first set of data points and the second set of data points, or both the first set of data points and the second set of data points and inputs generated from the first set of data points and the second set of data points.

8. The system of claim 6, wherein the restorative side of the customized pillow provides for a geometry, one or more contours, or both, which are configured to cradle a head of the individual at one or more of an angle, a flexed position, or an incline position, and wherein one of or more the angle, the flexed position, or the incline position, are, in whole or in part, determined by the system.

9. The system of claim 1, wherein the first scanner includes at least one of an infrared scanner, a digital scanner, or a 3D scanner, wherein the second scanner includes at least one of an infrared scanner, a digital scanner, a goniometer scanner, or a 3D scanner, and wherein a type of the first scanner is different than or the same as a type of the second scanner.

10. The system of claim 1, further comprising a forward head posture scan providing a third set of data points, and wherein the generated inputs are based on the first set of data points, the second set of data points, and the third set of data points.

11. The system of claim 1, wherein the processor, and the computer-readable medium having executable instructions stored thereon, such that, when the executable instructions are executed by the processor, the processor is further operative to: generate a virtual representation of all or a part of a body of the individual or a skeleton of the individual using information from the first set of data points and the second set of data points, the inputs generated from the first set of data points and the second set of data points, or both the first set of data points and the second set of data points and the inputs generated from the first set of data points and the second set of data points, related to one or more of said individual's: posture, body posture, head posture, kinetic chain, body ergonomics, body part ergonomics, skeletal ergonomics, musculoskeletal ergonomics, body part relationships, skeletal part relationships, skeletal abnormalities, posture abnormalities, weight distribution, areas of reduced pressure, areas of increased pressure, limb lengths, muscle weakness, asymmetries between body parts, or body abnormalities.

12. The system of claim 1, wherein the processor, and the computer-readable medium having executable instructions stored thereon, such that, when the executable instructions are executed by the processor, the processor is further operative to: generate a two-dimensional and/or a three-dimensional virtual model of the foot or feet of the individual, a spine of the individual, or a skeleton of the individual, using, in whole or in part, the first set of data points, the generated inputs based on the first set of data points, or both.

13. The system of claim 1, wherein the processor, and the computer-readable medium having executable instructions stored thereon, such that, when the executable instructions are executed by the processor, the processor is further operative to: generate a two-dimensional and/or a three-dimensional virtual model of the head-and-neck region of the individual, a spine of the individual, or a skeleton of the individual, using, in whole or in part, the second set of data points, the generated inputs based on the second set of data points, or both.

14. The system of claim 1, further comprising a pressure mapping scan operative to scan the one or more portions of the bottom of the foot or feet of the individual to supplement the first set of data points or to provide a third set of data points for generating inputs.

15. The system of claim 1, wherein the processor, and the computer-readable medium having executable instructions stored thereon, such that, when the executable instructions are executed by the processor, the processor is further operative to: automatically identify one or more of, anatomy, target anatomy, or anatomical landmarks, and wherein the automatically identified anatomy, target anatomy, or anatomical landmarks, are used to one or more of: (a) identify the one or more orthopedic needs of the individual, (b) further define the design of the customized pillow, or (c) select or assist with the electronic selection of the one or more materials to be used to make the customized pillow.

16. The system of claim 1, wherein the processor, and the computer-readable medium having executable instructions stored thereon, such that, when the executable instructions are executed by the processor, the processor is further operative to: determine, based on the first set of data points, the second set of data points, the generated inputs, or combinations thereof, a foot or feet structure of the individual, a head-and-neck region structure of the individual, biomechanics of the individual, body posture of the individual, cervical alignment of the individual, musculoskeletal relationships of the individual, or combinations thereof.

17. The system of claim 16, wherein the processor, and the computer-readable medium having executable instructions stored thereon, such that, when the executable instructions are executed by the processor, the processor is further operative to: use the determined foot or feet structure of the individual, the head-and-neck region structure of the individual, the biomechanics of the individual, the body posture of the individual, the cervical alignment of the individual, the musculoskeletal relationships of the individual, or the combinations thereof, to render or assist with rendering the customized virtual pillow to provide specific support, correction, or accommodation, to treat the one or more orthopedic needs of the individual.

* * * * *